United States Patent [19]

Kawashima et al.

[11] 4,312,231
[45] Jan. 26, 1982

[54] APPARATUS FOR GENERATING AND DETECTING AN ELECTROMAGNETIC ULTRASONIC WAVE

[75] Inventors: Katsuhiro Kawashima; Shoji Murota, both of Kitakyushu; Yukio Nakamori, Nakama; Hisao Suzuki, Kitakyushu, all of Japan

[73] Assignees: Nippon Steel Corporation; Mitsubishi Denki Kabushiki Kaisha, both of Tokyo, Japan

[21] Appl. No.: 55,298

[22] Filed: Jul. 6, 1979

[51] Int. Cl.³ ............................................. G01N 29/00
[52] U.S. Cl. ...................................................... 73/643
[58] Field of Search .......................................... 73/643

[56] References Cited

U.S. PATENT DOCUMENTS

3,460,063  8/1969  Honck et al. ................. 73/643 X
4,092,868  6/1978  Thompson et al. ................ 73/643
4,104,922  8/1978  Alers et al. ........................ 73/643

Primary Examiner—James J. Gill

[57] ABSTRACT

An apparatus for generating and detecting an electromagnetic ultrasonic wave in which a magnetic field generator forms a magnetic field at the surface area of one side of a conductive material, and an eddy current and impulse of a magnetic field are produced in the surface area by supplying a high frequency current pulse to an ultrasonic wave generating coil, the interaction therebetween producing an ultrasonic wave which travels in the conductive material and further, the eddy current resulting from the interaction between the formed magnetic field and a reflected ultrasonic wave being reflected by another side of the conductive material or the internal defect contained therein is detected by a detecting coil which is electromagnetically separated from the ultrasonic wave generating coil by a decoupling means.

14 Claims, 10 Drawing Figures

APPARATUS FOR GENERATING AND DETECTING AN ELECTROMAGNETIC ULTRASONIC WAVE

BACKGROUND OF THE INVENTION

The present invention relates to an apparatus for generating and detecting an electromagnetic ultrasonic wave which serves to carry out, in connection with a conductive material, the detection of internal defects, the judgement as to the type of a material and thickness measurement.

For performing the measurement concerning internal defects or the like, an ultrasonic measuring instrument and an electromagnetic ultrasonic measuring apparatus have been utilized. However, in order to use an ultrasonic measuring instrument provided with an ultrasonic vibrator of quartz or barium titanate, a material to be measured is required to have a smooth surface and water or oil for receiving an ultrasonic incident wave is necessary. Thus the usage of the instrument has been remarkably restricted under an unfavorable surface condition such as the presence of rust or a high temperature condition.

An electromagnetic ultrasonic measuring apparatus was known and disclosed in the Japanese patent publication No. 24867/1969. It has been generally considered that the realization of the practical usage of the apparatus is almost impossible since any conventional apparatus fails to provide an adequate efficiency in electromagnetical generation or detection of an ultrasonic wave and tends to produce a broad dead zone due to the occurrence of the magnetic induction between an ultrasonic wave generating coil and a detecting coil, thus causing the apparatus to be inoperative in a case where the thickness of the material is thin and the internal defect is located near the surface of the material. Generally, in an apparatus for generating and detecting an ultrasonic wave, a magnetic field is formed near the surface of one side of a conductive material and an eddy current is also generated therein by providing an ultrasonic wave generating coil to which a high frequency current pulse is supplied, to thereby cause the interaction therebetween to occur and the ultrasonic wave traveling in the material to generate and further, the eddy current generated in the surface area as a result of the interaction between the ultrasonic wave and the magnetic field is detected by a detecting coil which operates in accordance with the electromagnetic induction theory.

The detected signal obtained by the detecting coil in such electromagnetic ultrasonic measurement includes a transmission pulse or induction signal induced by the high frequency current pulse passing through the ultrasonic wave generating coil and a reflected echo consisting of the ultrasonic wave which is reflected within the material. The time zone covered by the transmission pulse is called, in an ultrasonic defect inspection, a dead zone due to the transmission pulse, which prevents the recognition of the presence of a reflected echo and preferably must be reduced.

Further, it has been desired to improve the detection sensitivity since a conventional electromagnetic ultrasonic measuring device produces a detection signal with poor sensitivity.

SUMMARY OF THE INVENTION

An object of the present invention is to reduce the dead zone due to a transmission pulse by electromagnetically separating an ultrasonic wave generating coil from a detecting coil in an apparatus for generating and detecting an electromagnetic ultrasonic wave.

Another object of the present invention is to reduce the dead zone due to a transmission pulse by preventing, in a detection circuit in an apparatus for generating and detecting an electromagnetic ultrasonic wave, the passage of a signal component having a frequency in the vicinity of the frequency of the current applied to an ultrasonic wave generating coil.

Another object of the present invention is to improve a detecting sensitivity by applying a high frequency current pulse having a large current value to an ultrasonic wave generating coil in an apparatus for generating and detecting an electromagnetic ultrasonic wave to thereby increase the amplitude of an electromagnetic ultrasonic wave propagating within a material to be measured.

Another object of the present invention is to improve a detection sensitivity by increasing the density of the magnetic field applied in the vicinity of an ultrasonic wave generating coil and a detecting coil in an apparatus for generating and detecting an eletromagnetic ultrasonic wave.

Another object of the present invention is to improve a S/N ratio of a detection signal by shutting out external noise which reaches a detecting coil in an apparatus for generating and detecting an electromagnetic ultrasonic wave.

Another object of the present invention is to miniaturize an apparatus for generating and detecting an electromagnetic ultrasonic wave.

A further object of the present invention is to improve the stability of discharge produced by a spark gap for generating an electromagnetic ultrasonic wave and to increase the life time of the spark gap.

The present invention is directed to an apparatus for generating and detecting an electromagnetic ultrasonic wave, which apparatus comprises: a magnetic field generator for generating a magnetic field applied to the surface area of one side of a conductive material, a high frequency pulse source for generating a high frequency current pulse, an ultrasonic wave generating coil for receiving the currrent pulse from the high frequency pulse source to produce an eddy current and a magnetic field pulse in the surface area of the one side of the conductive material or a surface area of the opposite side thereof, causing the interaction therebetween to generate an ultrasonic wave in the material, a detecting coil for detecting an eddy current which generates in the conductive material due to the interaction between the magnetic field formed by the magnetic field generator and an ultrasonic wave which is reflected by the opposite side of the conductive material or an internal defect or a surface defect contained in the conductive material or a transmitted ultrasonic wave propagated therethrough, a displaying apparatus for displaying a detection signal which is sensed by the detecting coil, and/or a decoupling means for reducing an amount of electromagnetic coupling between the ultrasonic wave generating coil and the detecting coil. Preferably provided at a stage following the detecting coil is a filter for eliminating a signal component in the detection signal having a frequency in the vicinity of the high frequency current pulse. Discharge electrodes and a capacitor may be connected between the high frequency pulse source and the ultrasonic wave generating coil. Furthermore, it is appropriate to continuously enclose the discharge electrodes by incombustible gas.

According to the present invention, reduction of the electromagnetic coupling between the ultrasonic wave generating coil and the detecting coil and elimination of the signal component having a frequency near that of the high frequency current pulse can be carried out to thereby reduce the dead zone due to the transmission pulse and to enable the application of the electromagnetic ultrasonic measurement to various objects to be measured and to improve measurement accuracy. The present invention can also increase the amplitude of the ultrasonic wave propagating within the conductive material and the strength or density of the magnetic field to be applied to the surface area of the conductive material, resulting in the improvement of detection sensitivity. The miniaturization of the generation/detection apparatus can be also achieved. Furthermore, the apparatus according to the present invention can permit the discharge electrodes to have stability in the discharging operation and a long life time in use thereof.

BRIEF DESCRIPTION OF THE DRAWINGS

FIGS. 6 and 7 are views for illustrating typical display waveforms of electromagnetic ultrasonic detection signals, wherein

DETAILED DESCRIPTION OF THE INVENTION

Figure 1:
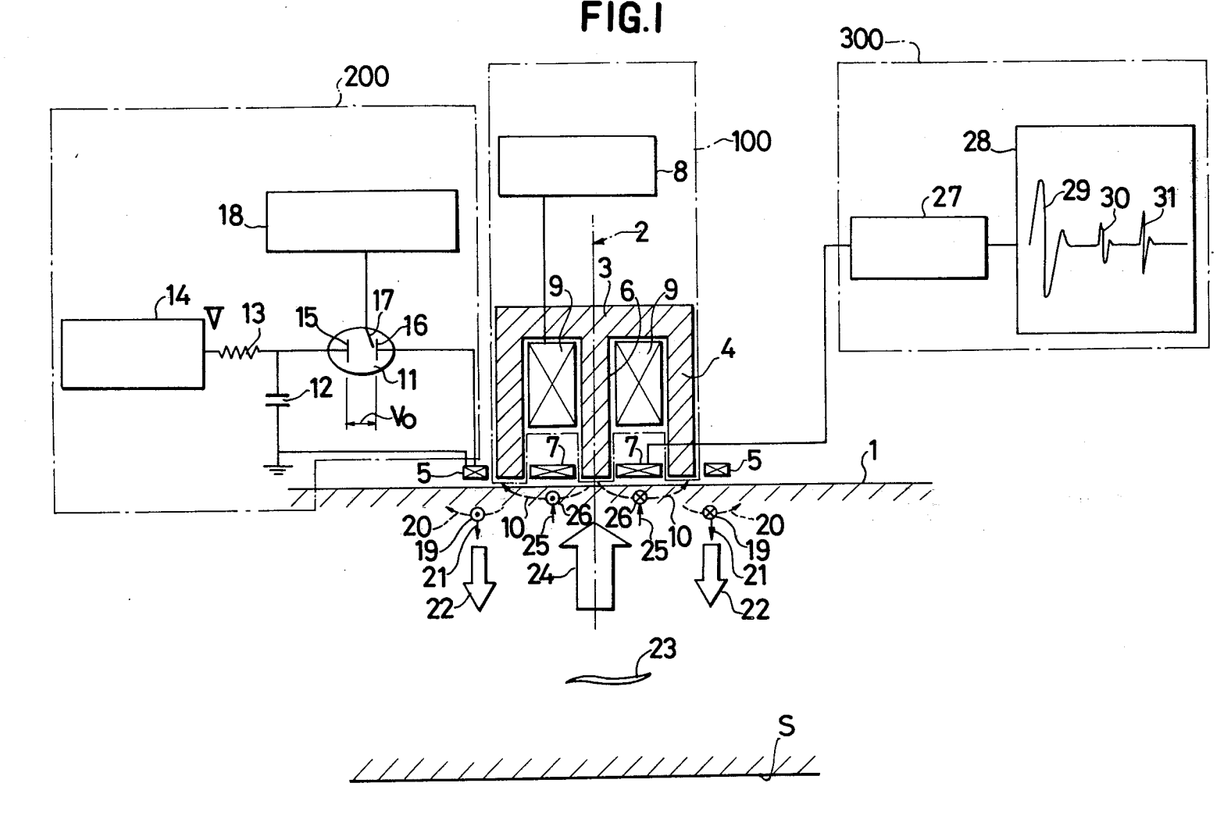
FIGS. 1–3 are schematic sectional views, partly illustrated by a block circuit diagram, showing apparatuses for generating and detecting an electromagnetic ultrasonic wave embodying the present invention and having different decoupling means, respectively.

Referring to the attached drawings, preferred embodiments of an apparatus for generating and detecting an electromagnetic ultrasonic wave according to the present invention will be explained hereinbelow. In FIG. 1 generalized construction in accordance with the present invention is shown. The apparatus comprises a magnetic field generator 100 for applying a magnetic field 10 to the surface of a conductive material 1, high frequency pulse source 200, an ultrasonic wave generating coil 5 for generating an eddy current 19 and a magnetic field pulse 20 in the material 1, a detecting coil 7 for detecting an eddy current 26, and a displaying apparatus 300 for displaying a detecting signal. As explained in the above, a principal feature of the present invention resides in that there is provided a decoupling means for reducing the degree of the electromagnetic coupling between the ultrasonic wave generating coil 5 and the detection coil 7. Thus, the decoupling means according to the present invention will be sufficiently discussed in the following.

Referring to FIG. 1, the ultrasonic wave generating coil 5 is positioned near the conductive material 1 and outside of a periphery magnetic pole 4 of a ferromagnetic magnet 3 having a rotational symmetric axis 2. The detecting coil 7 is positioned between the periphery magnetic pole 4 and a central magnetic pole 6. Then, both of coils 5 and 7 are electromagnetically separated with each other by the magnetic field generator 100, specifically by the periphery magnetic pole 4. That is, the periphery magnetic pole 4 serves as the decoupling means in this embodiment and can reduce a dead zone due to a transmission pulse. Further, the apparatus shown in FIG. 1 can be formed in smaller size such as 20 mm in diameter, 30 mm in length when compared with the conventional ones since it is not required to provide a large sized magnetic field generator to cover the electromagnetic ultrasonic wave generating coil or to form an external magnetic field for generating the ultrasonic wave.

When compared with the apparatus shown in FIG. 1, the apparatus according to FIG. 2 has different constructional features which are as follows: the magnet 3 further includes a intermediate magnetic pole 41; there are provided two magnetic field generating coils 91 and 92; the ultrasonic wave generating coil 5 is positioned between the periphery magnetic pole 4 and the intermediate magnetic pole 41 while the detecting coil 7 is positioned between the central magnetic pole 6 and the intermediate magnetic pole 41.

The features of this embodiment resides in that the intermediate magnetic pole 41 serves as the decoupling means to reduce the degree of the electromagnetic coupling between the both coils 5 and 7 to thereby reduce the dead zone and that the distance between respective magnetic poles is approximately ½ times as large as that in a conventional apparatus, resulting in increase in the strength of the magnetic field applied to the conductive material 1 which permits the improvement of the detection sensitivity. In addition, the S/N ratio of the detection signal can be improved since the intermediate magnetic pole 41 can substantially prevent the detecting coil 7 from being subjected to an external noise.

Figure 3:
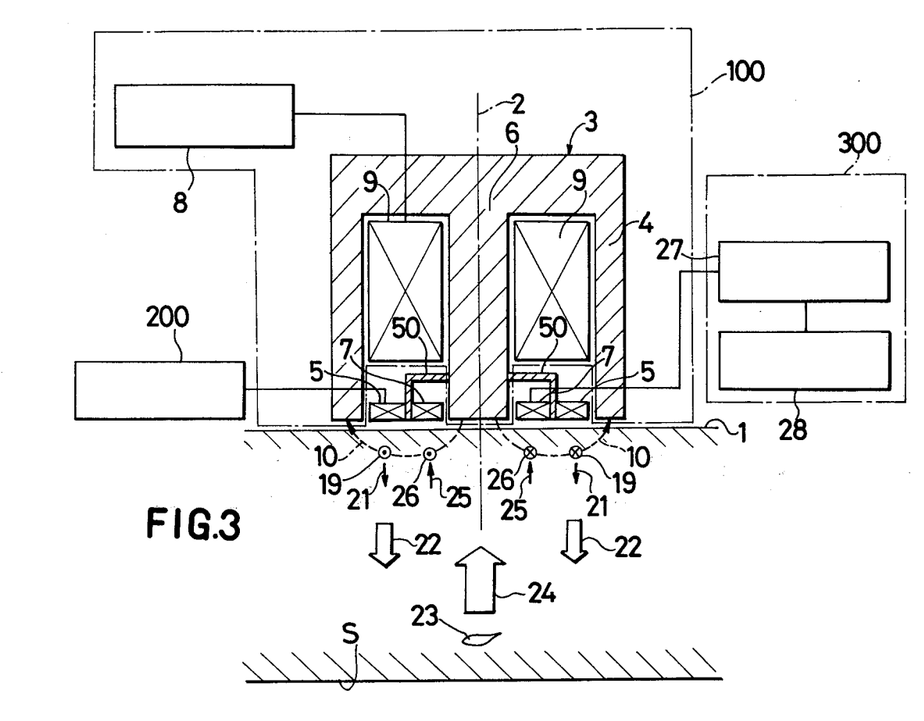

FIG. 3 is a schematic sectional view, partly explained in a block circuit diagram, showing another embodiment according to the present invention.

When compared with the apparatus shown in FIG. 1, the constructional feature of this embodiment resides in a point that both of the ultrasonic wave generating coil 5 and the detecting coil 7 are positioned between the periphery magnetic pole 4 and the central magnetic pole 6 and that a non-magnetic metal separating wall 50 is provided between the coils 5 and 7 to electromagnetically separate the coils 5 and 7 from each other. Thus, the separating wall 50 serves as the decoupling means causing the dead zone to decrease. The separating wall 50 also prevents the external noise from reaching the detecting coil 7 to improve the S/N ratio of the detection signal.

Figure 4:
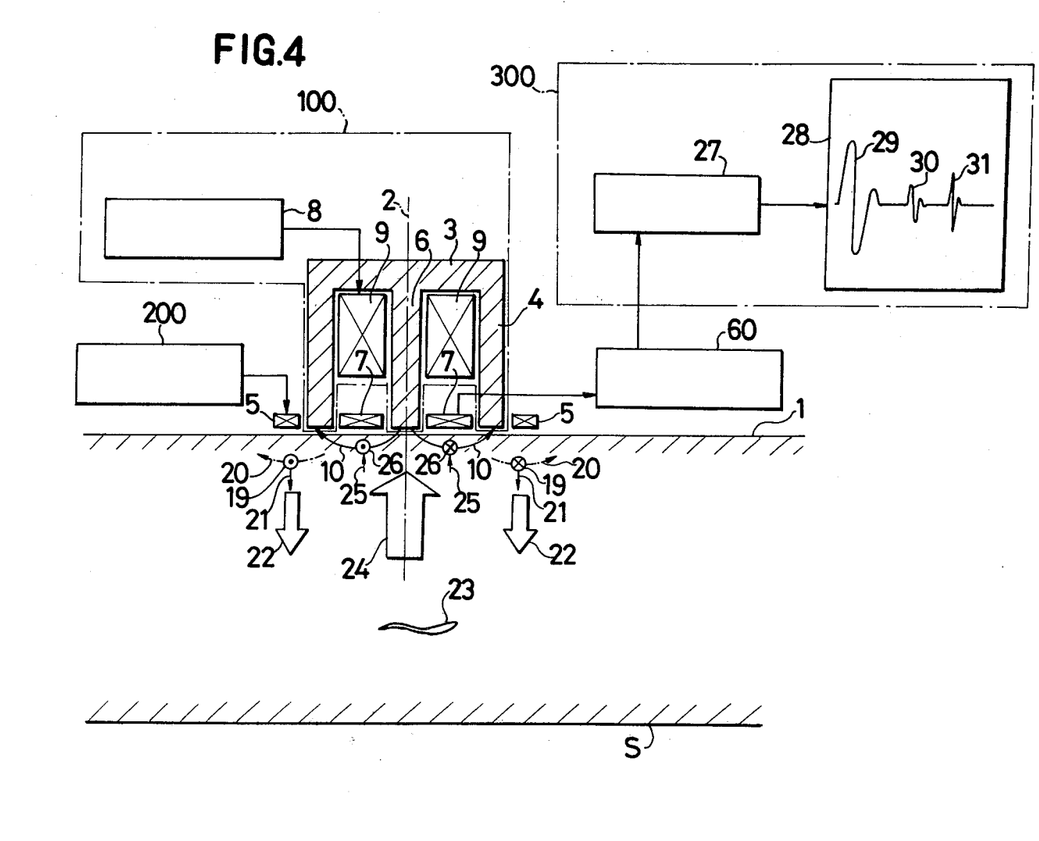
FIG. 4 is a schematic sectional view, partly illustrated by a block circuit diagram, showing an apparatus for generating and detecting an electromagnetic ultrasonic wave provided with a filter embodying the present invention.

Referring to FIG. 4, another embodiment will be explained hereinbelow.

As with the above-mentioned apparatuses, the embodiment shown in FIG. 4 attempts to reduce the dead zone and the features thereof resides in that a filter 60 is provided at a stage prior to the displaying apparatus 300 to prevent a signal component in the detection signal having a substantially the same frequency as that of the high frequency current pulse from being introduced to the apparatus 300 while the ultrasonic wave generating coil 5 and the detecting coil 7 are electromagnetically separated from each other.

The present inventors found that the frequency of the ultrasonic wave resulting from the interaction between the magnetic field pulse and the eddy current is twice times as large as that of the high frequency current pulse and that the dead zone can be remarkably reduced and the S/N ratio of the detection signal can be improved by providing the above-mentioned filter 60. Further explanations concerning the findings will be shown in detail hereinafter.

Assuming the pulse of current applied to the ultrasonic wave generating coil 5 has a central frequency $f_o$, in a short time period during which the pulse of current is kept to flow, the current pulse is approximately presented by:

$$I = I_o \cos(2\pi f_o t + \phi_1)$$

, wherein $I_o$ is the amplitude of the current pulse.

The eddy current pulse 19 is given by:

$$I_E = K_E I_o \cos(2\pi f_o t + \phi_2)$$

The magnetic field pulse 20 is also given by:

$$B = K_B I_o \cos(2\pi f_o t + \phi_3)$$

, wherein $K_E$, $K_B$ are coefficients and $\phi_1$, $\phi_2$, $\phi_3$ show phases, respectively.

Following the Lorentz's Law, the vibration force 21 can be expressed by:

$$F = I_E \times B$$
$$= K_B K_E I_o^2 \cos(2\pi f_o t + \phi_2)\cos(2\pi f_o t + \phi_3)$$
$$= \tfrac{1}{2} K_E K_B I_o^2 \cos[(2\pi(2f_o) t + \phi_2 + \phi_3) + \cos(\phi_2 + \phi_3)]$$

Thus, it can be found that the magnitude of the vibration force 21 is proportional to the square of the amount of the current pulse applied to the ultrasonic wave generating coil 5 and the frequency thereof is twice times as that of the current pulse. Therefore, frequencies of a defect waveform 30 and a bottom surface waveform 31 are also twice times as large as that of the transmission pulse waveform 29.

The filter 60 is a band-pass-filter for preventing the passage of the signal component having substantially the same frequency as that of the transmission pulse and permitting the passage of the signal component having a frequency which is approximately twice times as large as the transmission pulse toward the displaying apparatus 300, which filter 60 can reduce the dead zone and eliminate an unfavorable phenomenon such that the defect waveform 30 and the bottom surface waveform 31 can be hidden behind the dead zone.

As explained in the above, several constructions in accordance with the present invention for reducing the dead zone have been shown. In order to provide more appropriate construction respective constructions mentioned above can be combined since there is no requirement to use same separately.

Referring to FIG. 1 again, constructions for improving the detection sensitivity will be explained.

As discussed in connection with the apparatus shown in FIG. 4, the strength of an ultrasonic wave propagating in the conductive material 1 is in proportion to the square of the high frequency current pulse. Thus, the applicaton of the high frequency current pulse having a large current value is required to increase the strength of the ultrasonic wave and to thereby enhance the detection sensitivity. A high frequency pulse source 200 discussed below is a preferred embodiment according to the present invention to realize such requirement.

In FIG. 1, the ultrasonic wave generating coil 5 is connected with a capacitor 12 through a trigger type discharging electrode 11, the capacitor 12 being supplied with a high D.C. voltage V from a high voltage supply 14 through a charging resistance 13. The trigger type discharging electrode 11 is provided with a triggering electrode 17 in the vicinity of discharging electrodes 15 and 16 which are positioned face-to-face relationship with each other, the triggering electrode 17 being connected with a triggering pulse supply 18. Normally, the discharging electrodes 15 and 16 are electrically opened and cause discharge to occur therebetween when the potential difference between the electrodes 15 and 16 reaches a predetermined value $V_o$ and thereby being conductive state. In case that the output voltage V from the high voltage supply 14 is set to be slightly lower than the predetermined value $V_o$, the capacitor 12 is charged to the voltage level V through the charging resistance 13. Under such condition, the application of a triggering pulse to the triggering electrode 17 by actuating the triggering pulse supply 18 can induce the discharge between the discharging electrodes 15 and 16, this permitting an electric energy stored in the capacitor 12 to flow into the ultrasonic wave generating coil 5 in the form of a high frequency current pulse.

The following apparatus concerns the discharging electrodes 15, 16 which are preferably provided in the high frequency pulse supply 200 to produce the advantages explained in the above, and the apparatus is designed to receive the discharging electrodes in a manner the electrodes are continuously surrounded by a incombustible gas to thereby realize getting the stability of the discharge during operation and a long life time.

Figure 5:
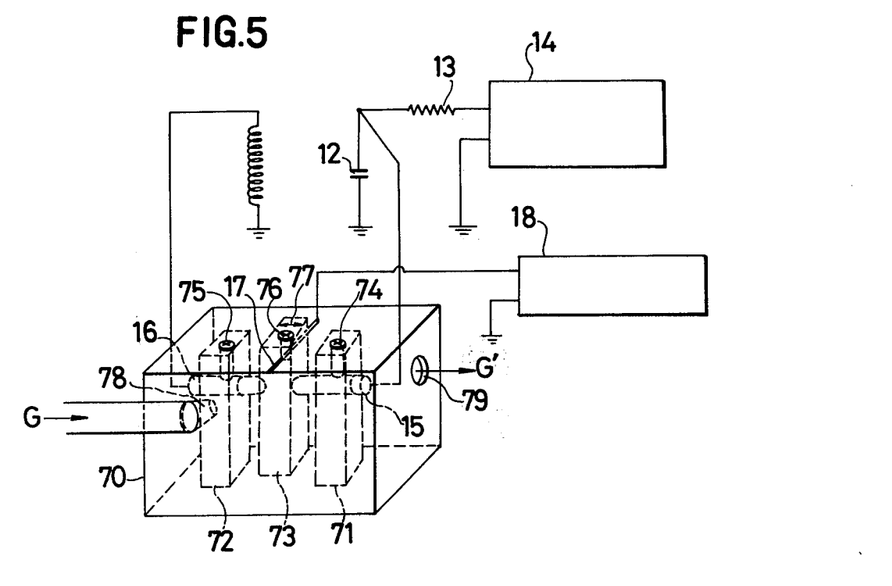
FIG. 5 is a schematic perspective view, partly illustrated by a block circuit diagram, showing a gas-blowing type spark gap for generating an electromagnetic ultrasonic wave suitable for the apparatus according to the present invention.

FIG. 5 is a schematic view illustrating the constructions and functions of a spark gap for generating an ultrasonic wave used for the apparatus according to the present invention. In a container 70, the discharging electrodes 15, 16 are positioned so that both electrodes 15, 16 opposite to each other and the triggering electrode 17 is arranged near the discharging electrodes 15 and 16. These electrodes are supported by fixing frames 71, 72, and 73 at the bottom of the container 70 and the distance therebetween can be adjusted and fixed by using distance adjusting screws 74, 75, 76 so that desirable distances can be obtained. The fixing frame 73 for the triggering electrode 17 is movable in both directions shown by an arrow 77. The container 70 comprises a inlet port 78 through which incomstible gas G blows into the container 70 and directs to the discharging electrodes 15 and 16 and an outlet port 79 for exhausing gas G'. A small amount of the incombustible gas G such as $N_2$ and Ar or the like is continuously introduced through the inlet port 78 while exhausting same from the outlet port 79. After filling the inner space of the container 70 with the incombustible gas which excludes air contained therein, a small amount of the incombustible gas is continuously and constantly supplied and exhausted.

The above-mentioned constructions can maintain a constant peripheral environment about the discharging electrodes 15, 16 to substantially eliminate the affection of the changes in the pheripheral conditions such as the amounts of humidity and fine particulate dusts. Further, in the present invention, the damage due to the high temperature resulting from the occurrence of sparking between the electrodes 15, 16 can be entirely eliminated from the practical viewpoint and there is no requirement for making careful consideration as to the possibility of firing or explosion of combustible materials near the spark gap, since the spark generated during the discharging operation is enclosed by nitrogen gas.

The generalized features and specific embodiments of the present invention have been discussed, hereinabove.

It can be noted that the present invention attempts to achieve the provision of the apparatus constructions realizing the reduction of the dead zone. In addition to this, the present invention proposes several novel constructions to solve problems which appear in conventional ultrasonic measuring instruments. Useful measuring apparatus can be provided by suitably combining the constructions disclosed in the above.

The operation of an apparatus according to the present invention will be explained based upon the typical apparatus shown in FIG. 1.

A magnetic field 10 extending in the radial and horizontal directions generates in the conductive material 1 when the magnetic field generating coil 9 receives a voltage from a voltage supply 8. The magnetic field 10 is confined to inside the peripheral magnetic pole 4 in view of the construction of the magnet 3. A high frequency current pulse is supplied to the ultrasonic wave generating coil 5 by operating the triggering electrode 17 after charging the capacitor 12 up to the predetermined voltage V.

The flow of the high frequency current pulse in the generating coil 5 induces the pulse of a circular eddy current 19 formed in the conductive material 1 and in parallel with the surface thereof and the pulse of a magnetic field 20. The eddy current pulse 19 and the magnetic field pulse 20 interact with each other to produce a vibrating force 21 in the vertical direction as shown by an arrow following Fleming's left-hand rule, which force 21 propagating as an electromagnetic ultrasonic wave in the direction shown by an arrow 22. When the electromagnetic ultrasonic wave reaches the bottom surface S of the conductive material 1 or an internal defect 23 therein, it is reflected in the direction shown by an arrow 24. The reflected ultrasonic wave produces a vibrating force 25 in the vicinity of the upper surface of the material 1.

Following Fleming's right-hand rule, the interaction between the vibrating force 25 and the magnetic field 10 generates an eddy current 26 which is detected by the detecting coil 7 and is amplified by an amplifier 27, the waveform thereof being displayed on an displaying device 28 such as a synchroscope. In the displaying device, firstly appeared is a waveform of an initial pulse 29 which is based on the current flowing in the detecting coil 7 which is induced by the high frequency current pulse in the ultrasonic wave generating coil 5. Next, a waveform 30 representing the internal defect 23 and a waveform 31 corresponding to the bottom surface appear, successively.

Figure 2:
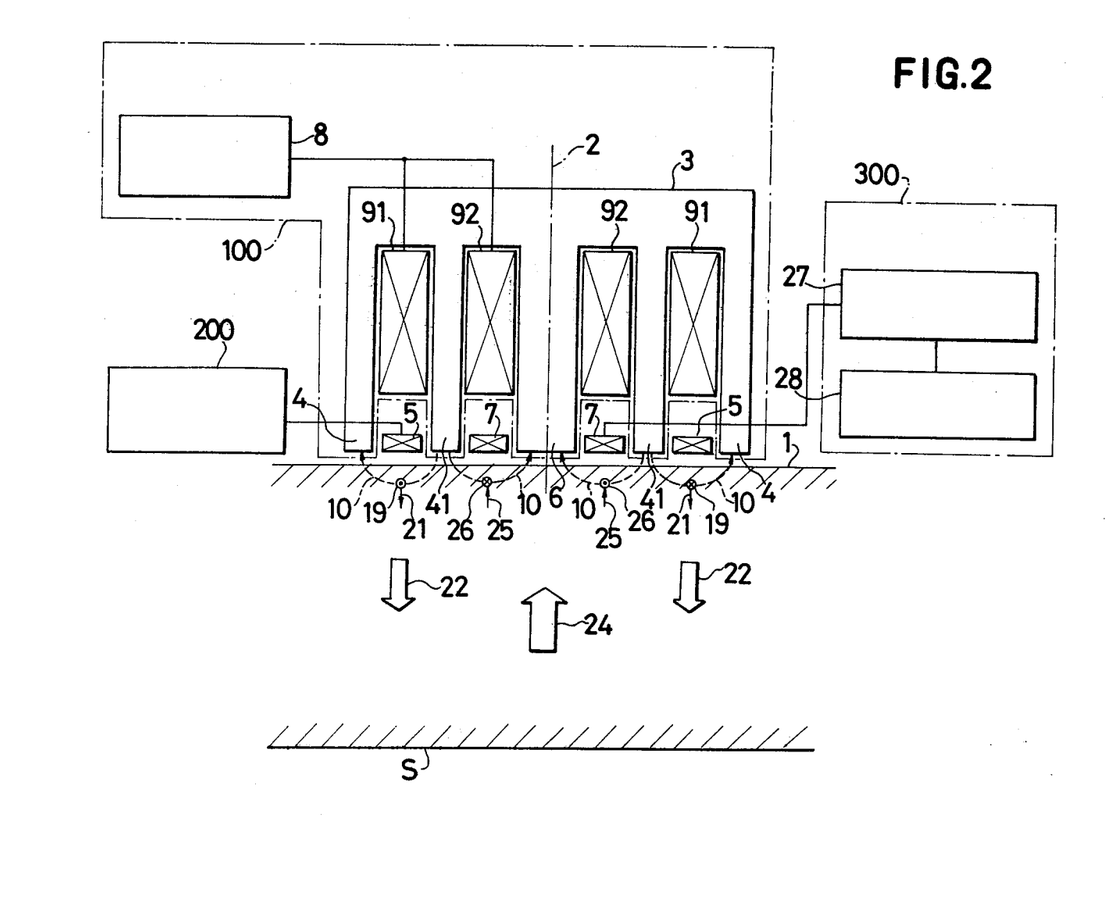

In this situation, provision of the decoupling means shown in FIGS. 1–3 or the filter shown in FIG. 4 or both permits the reduction of the dead zone due to the transmission pulse.

Next, a modification of the apparatus indicated in FIG. 1 will be illustrated.

In the above-mentioned embodiment, there is shown the ferromagnetic magnet having the rotational symmetric axis, however, it is not required for the magnet to have such rotational symmetric axis. Also, a permanent magnet may be, of course, utilized in place of using the electromagnet. In the modification of the preferred embodiment previously explained having the peripheral magnetic pole 4 and the central magnetic pole 6, there is no specific requirement or restriction except that the generating coil 5 should be positioned outside the magnet for generating detection magnetic field and the detecting coil 7 should be positioned inside thereof to electromagnetically separate both coils 5 and 7 with each other, therefore, any type of configurations can be used. Instead of using the trigger type discharging electrode 11, by raising the output voltage from the high voltage supply 14 above $V_o$, a natural discharge between the electrodes 15 and 16 may be caused to generate. It is not an essential requirement whether or not the electrodes 15, 16 are enclosed by glass or ceramics or the like. Further, a cathode-heating type discharging tube using thermoelectrons can be also utilized as the discharging electrodes in place of a pair of metallic or carbon bars which are not subjected to heating.

In the following, modifications of the apparatus shown in FIG. 2 will be shown.

Although the rotational axissymmetric shaped apparatus is disclosed previously, another type of apparatus, for example, rectangular shaped apparatus may be used responsive to the shapes of the generating coil 5 and the detecting coil 7.

While the disclosed embodiment relates to a longitudinal utltrasonic measuring method, the electromagnetic ultrasonic wave generating and detecting apparatus having the intermediate magnetic pole 41 positioned between the coils 5 and 7 can be applied to a surface wave measuring method. Of course, a permanent magnet or an electromagnet can be used as the magnet 3. The thickness of the tip of the intermediate pole 41 can be varied in response to the dimension of the generating and detecting apparatus.

Modification of the apparatus shown in FIG. 3 can be made as explained below. The metallic separating wall 50 is preferably formed of brass and may also consist of a non-magnetic conductive metal such as stainless steel, aluminium or the like. The thickness of the wall can vary from about 0.8 mm to 5 mm not to produce remarkable loss in the strength of the external magnetic field. Illustrated is a longitudinal ultrasonic measuring method, however, in case the generating and detecting apparatus is capable of providing the metallic separating wall 50 between the generating coil 5 and the detecting coil 7, the application thereof to an apparatus using a transversal or surface ultrasonic wave can be carried out. The configuration of the apparatus may be changed to obtain a desirable shape such as the rotational axissymmetric or rectangular shape in response to the configuration of the coils 5 and 7.

The following is an explanation of the modification of the apparatus shown in FIG. 4.

In the embodiment, there is provided the band-pass-filter for selectively passing the signal component having the frequency in the vicinity of the square of that of the initial pulse waveform 29. Instead of doing this, it is also suitable to use a band-reject-filter preventing the signal component having the frequency in the vicinity of that of the initial pulse waveform 29 to pass and to use a high-pass-filter allowing the signal component having a frequency above the square of the frequency of the initial pulse waveform 29 to flow.

Finally, the modifications of the apparatus shown in FIG. 5 will be shown.

The technical art disclosed in the embodiment including the triggering electrode can be applied to the spark gaps in which a pair of fixed electrodes is provided or one of electrodes is movable and a rotating-plate type spark gap. The electrode can be constructed by a conductive metal such as stainless steel instead of using tungsten. The kind of the gas to be supplied to the container 70 is not specifically restricted except that same should be of incombustible one.

As explained above, the present invention can be applied to a surface wave method and a transmission method as well as a reflection method.

Figure 8:
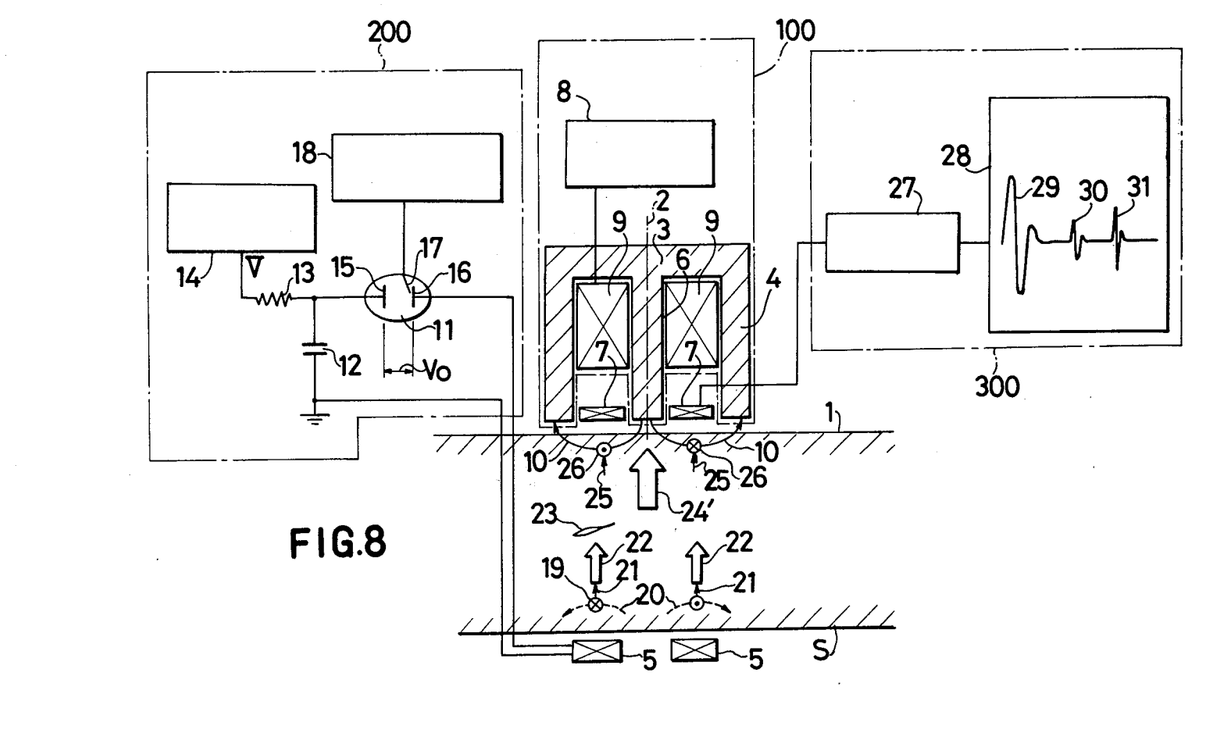
FIG. 8 is a schematic sectional view, partly illustrated by a block circuit diagram, showing a modification of the apparatus shown in FIG. 1 or the application of the invention to a transmission method.

There is shown, in FIG. 8, an apparatus for carrying out the application of the present invention to a transmission method, wherein the magnetic field generator 100 and the detecting coil 7 among the apparatus components illustrated in FIG. 1 are arranged close to the one side of the material 1 to be measured while the ultrasonic wave generating coil 5 is arranged opposite to the coil 7 and close to the another side thereof. According to such constructions, thickness measurement can be carried out by reading the time difference between a transmission pulse and a detected pulse appeared on the displaying apparatus and the judgement as to whether or not there is an internal defect in the material can be carried out by finding the degree of attenuation in the strength of a transmitted pulse. A reference numeral 24' designates a transmitted ultrasonic wave and other numerals are used as in FIG. 1. The apparatus of this embodiment is not required to have a magnetic field generator for ultrasonic wave generation, permitting the miniaturization of the apparatus.

In case of the application to the surface wave method, which is not shown in the drawings, a pulse of a magnetic field is formed in the direction perpendicular to the material surface. The interaction of the pulse with an eddy current produces an ultrasonic wave propagating along the surface of the material, the ultrasonic wave reflected by a surface defect being detected.

In the following, several examples embodying the present invention will be shown.

EXAMPLE I

Firstly, Example I corresponding to the apparatus shown in FIG. 1 is illustrated.

A high voltage supply 14 was of a voltage rating 20 KV and a power rating 300 VA. A capacitor 12 had a capacitance of 0.01 μF. A trigger type discharging electrode 11 was provided with a pair of discharging electrodes 15, 16 embedded in a ceramics material and a triggering electrode 17. Then, an ultrasonic wave generating coil 5 was connected in series with the electrode 11 to produce a high frequency current pulse with a frequency of 2 MHZ and an amplitude of 2 KA in the coil 5 which induces an ultrasonic wave providing a practically sufficient strength. In order to form a magnetic field for detection, the magnetomotive force of a magnetic field generating coil 9 was set as 1500 amperaturn, thereby producing a magnetic field of 2 KG in the vicinity of a steel material of which surface temperature being approximately 1000° C. As a result of using the above-mentioned constructions, practically sufficient detection sensitivity can be obtained, specifically, ±0.5 mm accuracy in the thickness measurement of the steel to be measured can be achieved and an internal defect located in the depth of 40 mm and being 3 mm in diameter can be detected.

EXAMPLE II

Example II corresponds to the apparatus indicated in FIG. 2. The electromagnetic ultrasonic generation/detection apparatus was of 90 mm in an outer diameter and 100 mm in height. A high frequency pulse supply had a voltage rating of 20 KV and power rating of 300 VA to which a capacitor of 0.01 μF and a trigger-type spark gap and an ultrasonic wave generating coil 5 were connected in series circuit relationship to thereby obtain a pulse of current, of which frequency being 1 MHZ and amplitude being 2 KA, in the coil 5. A magnetic field generating coils 91, 92 of which magnetomotive force being 12,000 AT were used to form a magnetic field of 5 KG between a central magnetic pole 6 and an intermediate magnetic pole 41 and between the intermediate pole 41 and a peripheral magnetic pole 4. As a sample to be measured, a SUS 27 with 100 mm thickness was used. The tip portion's thickness of the intermediate pole 41 was determined as 2.0 mm after considering the detection sensitivity and the ease in practical usage.

Figure 6A:
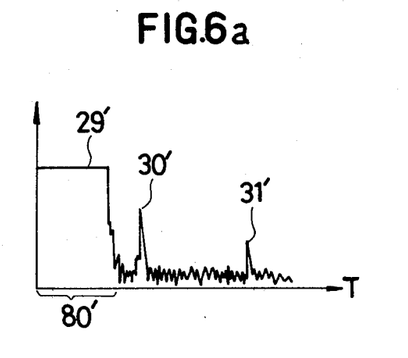
FIGS. 6(a) and 7(a) show display waveforms obtained by conventional apparatuses and FIGS. 6(b) and 7(b) show display waveforms obtained by apparatuses shown in FIG. 2 and FIG. 3, respectively.
Figure 6B:
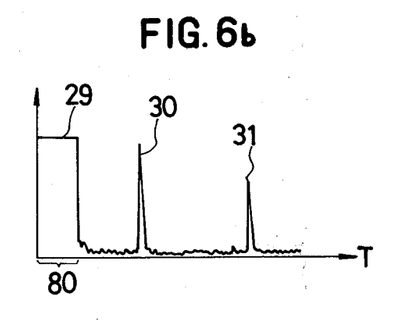

Next, under these conditions, displayed waveform of an electromagnetic ultrasonic detection signal obtained by using a storage type synchroscope as a displaying device 28 will be shown in FIG. 6. FIG. 6 schmatically shows the displayed waveform of the detection signal in which the strength of the detection signal is taken along the axis of ordinates and the propagating time of the ultrasonic wave is taken along the axis of abscissa. FIG. 6(a) shows the waveform obtained by using a conventional electromagnetic ultrasonic generation/detection apparatus while FIG. 6(b) shows the waveform obtained by the apparatus according to Example II. The respective waveform consists of a transmission pulse 29' or 29, a first reflection echo 30' or 30, and a second reflection echo 31' or 31 and a part designated by a reference numeral 80' or 80 shows a dead zone.

As noted above, utilization of the electromagnetic ultrasonic generation/detection apparatus can permit the remarkable reduction of the dead zone and the considerable enhancement of the detection sensitivity to produce great advantages. Therefore, practicality of the ultrasonic measuring instrument is greatly improved as a result of the realization of the detection of the signal which cannot detected by a conventional apparatus and the improvement of the detection sensitivity.

EXAMPLE III

Next example concerns the apparatus shown in FIG. 3.

An electromagnetic ultrasonic wave generation/detection apparatus provided with a metallic separating wall was used together with a high frequency pulse source of which voltage and power ratings were 20 KV and 300 VA, respectively. A capacitor of 0.01 μF, a trigger type spark gap, and an ultrasonic wave generating coil 5 were connected in series with the pulse source to produce a pulse of current with 1 MHZ frequency and 2 KA amplitude in the coil 5. At the same time, a 10,000 AT magnetic field generating coil 9 was used to form a 3 KG magnetic field 10 applied to a sample which was of a SUS 27 having 100 mm thickness.

Figure 7A:
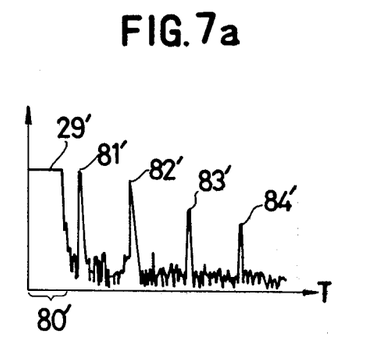
Figure 7B:
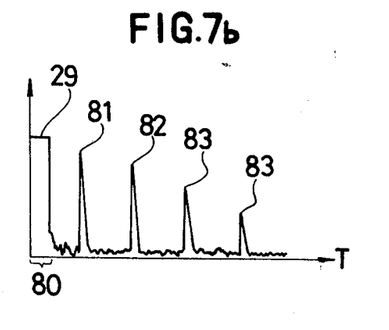

A displayed waveform is shown in FIG. 7, which waveform was obtained under the above-mentioned conditions and displayed on a storage type synchroscope or displaying device 28 for indicating an electromagnetic ultrasonic detection signal. In FIG. 7, the ordinate axis represents the strength of an ultrasonic detection signal while the abscissa axis represents the propagating time of an ultrasonic wave. FIGS. 7(a) and 7(b) show respective waveform obtained by an apparatus without a metallic separating wall 50 and an apparatus provided with the wall, respectively. The respective waveform consists of a transmission pulse 29' or 29, a first reflection echo 81' or 81, a second reflection echo 82' or 82, a third reflection echo 83' or 83, and a fourth reflection echo 84' or 84. The time zone covered by the transmission pulse 29' or 29 is generally called as a dead zone designated by a numeral 80' or 80.

In case of providing the metallic separating wall 50 as shown in FIG. 7(b), a useful apparatus characterized by the great reduction of the dead zone and the improvement of the S/N ratio in the detection signal can be provided.

EXAMPLE IV

The following Example corresponds to the measuring apparatus shown in FIG. 4.

A high frequency pulse supply with 20 KV voltage rating and 300 VA power rating was utilized along with a capacitor, of which capacitance being 0.01 μF, and a trigger-type discharging electrode having a pair of discharging electrodes embedded in ceramics and a triggering electrode with which an ultrasonic wave generating coil 5 was connected in series circuit relationship. This results in generating of a pulse of current having a frequency of 2 MHZ and an amplitude of 2 KA to produce an electromagnetic ultrasonic wave of which frequency being 4 MHZ which can be considered as having enough strength in practical use. A 2 KG magnetic field for detection was formed in the vicinity of a steel heated up to a high temperature by using a 1,500 AT coil and a band-pass-filter for preventing the passage of a signal component near 2 MHZ. This results in decreasing of a dead zone to approximately one-thirds times as large as usual one and the achievement of the thickness measurement of a steel heated to approximately 1000° C. with accuracy of ±0.5 mm and the realization of the detection of an internal defect located at the depth of 40 mm and having 3 mm in diameter.

EXAMPLE V

The following concerns the apparatus shown in FIG. 5. Nitrogen was supplied to a container 70 through a gas blowing-in port 27 at a flow rate of 0.2 m$^3$/min. and at a pressure of 1.5 Kg/cm$^2$. A 5 mm diameter tungsten bar and a 1 mm diameter tungsten bar were used as discharging electrodes 15, 16 and a triggering electrode 17, respectively, the distance between the discharging electrodes being 10 mm. A voltage supply produces a d.c. voltage of 20 KV and resistor having resistance of 2 MHZ and a capacitor having capacitance of 0.1 μF were provided. Then, a triggering pulse of which voltage being 10 KV was supplied to produce stable discharge between the electrodes 15, 16 and to thereby produce an adequately large high frequency pulse current.

What is claimed is:

1. An apparatus for generating and detecting an electromagnetic ultrasonic wave, comprising:
   a magnetic field generator for generating a magnetic field applied to a surface are of one side of a conductive material;
   a high frequency pulse source for generating a high frequency current pulse;
   an ultrasonic wave generating coil for receiving said current pulse from said high frequency pulse source to produce a first eddy current and a magnetic field pulse in the surface area of said conductive material and for generating an ultrasonic wave in the conductive material, which ultrasonic wave generates resulting from interaction between said first eddy current and the magnetic field pulse;
   a detecting coil for detecting a second eddy current which generates in the surface area of the conductive material as a result of interaction between the magnetic field formed by the magnetic field generator and an ultrasonic wave reflected by another side of the conductive material or an internal defect contained in the conductive material;
   a displaying apparatus for displaying a detecting signal detected by the detecting coil;
   said detecting coil being positioned peripherally around a central magnetic pole of said magnetic field generator, and decoupling means peripherally positioned around the outer perimeter of said detecting coil and said ultrasonic wave generating coil being positioned peripherally around the outer perimeter of said decoupling means.

2. An apparatus as recited in claim 1, wherein the magnetic field generator is utilized as the decoupling means, the ultrasonic wave generating coil is positioned outside the magnetic field generator and the detecting coil is positioned inside thereof.

3. An apparatus as recited in claim 1, wherein the magnetic field generator includes an intermediate magnetic pole positioned between the ultrasonic wave generating coil and the detecting coil to serve as the decoupling means.

4. An apparatus as recited in claim 3, wherein the magnetic field generator further includes a peripheral magnetic pole arranged outside the intermediate magnetic pole and a central magnetic pole arranged inside the intermediate magnetic pole, the ultrasonic wave generating coil is positioned between the peripheral magnetic pole and the intermediate magnetic pole, and the detecting coil is positioned between the intermediate magnetic pole and the central magnetic pole.

5. An apparatus as recited in claim 1, wherein a separating wall of non-magnetic metal which serves as the decoupling means is provided between the ultrasonic wave generating coil and the detecting coil.

6. An apparatus as recited in claim 5, wherein the separating wall has a thickness varying from approximately 0.5 mm to 5 mm.

7. An apparatus as recited in any of claims 1 through 5, wherein further comprising a filter electrically connected between the detecting coil and the displaying apparatus for eliminating a signal component in the detection signal having a frequency near the frequency of the current pulse from the high frequency pulse source.

8. An apparatus as recited in claim 7, wherein the filter includes a band-pass-filter permitting a signal component in the detection signal to pass, the signal component having a frequency which is substantially the same as the square of that of the high frequency current pulse.

9. An apparatus as recited in any of claims 1 through 5, wherein the high frequency pulse source includes discharging electrodes and a capacitor connected with a high voltage supply in the high frequency pulse source and the ultrasonic wave generating coil, the high voltage supply charging the capacitor, an electric charge stored in the capacitor being supplied to the ultrasonic wave generating coil through the discharging electrodes.

10. An apparatus as recited in claim 9, wherein further comprising: a container having an inlet for continously receiving incombustible gas and outlet for exhausting the gas, and housing the discharge electrodes therein to thereby cause the electrodes to be continuously surrounded by the incombustible gas.

11. An apparatus as recited in claim 9, wherein the high frequency pulse source includes a trigger-type discharging electrode having two discharging electrodes and a triggering electrode and a triggering pulse source connected to the triggering electrode.

12. An apparatus as recited in claim 1, wherein the magnetic field generator is provided with an electromagnetic including a magnetic pole and a coil for generating the magnetic field applied to the surface area of the conductive material.

13. An apparatus as recited in claim 12, wherein the magnetic pole is formed into a shape having a rotational symmetric axis.

14. An apparatus as recited in claim 1, wherein the magnetic field generator is provided with a permanent magnet.

* * * * *